(12) United States Patent
Goto (10) Patent No.: US 10,869,670 B2
(45) Date of Patent: Dec. 22, 2020

(54) PROCEDURE FOR ENDOSCOPIC FULL-THICKNESS RESECTION

(71) Applicant: OLYMPUS CORPORATION, Hachioji (JP)

(72) Inventor: Osamu Goto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 346 days.

(21) Appl. No.: 15/935,419

(22) Filed: Mar. 26, 2018

(65) Prior Publication Data

US 2019/0290282 A1 Sep. 26, 2019

(51) Int. Cl.
| | |
|---|---|
| *A61B 17/11* | (2006.01) |
| *A61B 1/313* | (2006.01) |
| *A61B 17/04* | (2006.01) |
| *A61B 1/018* | (2006.01) |
| *A61B 17/32* | (2006.01) |
| *A61B 17/3209* | (2006.01) |
| *A61B 17/00* | (2006.01) |

(52) U.S. Cl.
CPC .......... *A61B 17/1114* (2013.01); *A61B 1/018* (2013.01); *A61B 1/313* (2013.01); *A61B 17/0469* (2013.01); *A61B 17/3209* (2013.01); *A61B 17/320016* (2013.01); *A61B 2017/0034* (2013.01); *A61B 2017/00269* (2013.01); *A61B 2017/1121* (2013.01); *A61B 2017/320056* (2013.01)

(58) Field of Classification Search
CPC ..... A61B 17/1114; A61B 1/018; A61B 1/313; A61B 17/3209; A61B 2017/00269
See application file for complete search history.

(56) References Cited

U.S. PATENT DOCUMENTS

| | | | | |
|---|---|---|---|---|
| 5,151,086 A | * | 9/1992 | Duh | A61B 17/0281 604/506 |
| 6,346,111 B1 | * | 2/2002 | Gordon | A61B 17/0469 606/139 |
| 7,571,729 B2 | * | 8/2009 | Saadat | A61B 17/0401 128/898 |
| 7,704,264 B2 | * | 4/2010 | Ewers | A61B 1/00135 606/151 |
| 8,066,689 B2 | * | 11/2011 | Mitelberg | A61B 1/00165 604/509 |

(Continued)

FOREIGN PATENT DOCUMENTS

| | | |
|---|---|---|
| JP | 2007-029195 A | 2/2007 |
| JP | 2007-508053 A | 4/2007 |
| WO | 2005/037152 A1 | 4/2005 |

*Primary Examiner* — Timothy J Neal
*Assistant Examiner* — Jae Woo
(74) *Attorney, Agent, or Firm* — Oliff PLC (57) ABSTRACT

A method of resecting entire layers of a digestive tract includes: an insertion step of inserting an endoscope into the digestive tract; an everting step performed after the insertion step, to suture mucosal layers located on both sides of a target region including a lesion, cover the target region with the mucosal layers, and evert a tract wall including the target region to a side of an abdominal cavity, in the digestive tract; and an incision step performed after the everting step, to position an incision tool between the target region and the mucosal layers to incise the tract wall around the lesion by the incision tool.

12 Claims, 9 Drawing Sheets

(56) References Cited

U.S. PATENT DOCUMENTS

| | | | |
|---|---|---|---|
| 8,771,170 B2* | 7/2014 | Mesallum | A61B 17/0218 600/104 |
| 9,039,649 B2* | 5/2015 | Neisz | A61F 2/04 604/264 |
| 9,278,019 B2* | 3/2016 | Thompson | A61F 2/04 |
| 9,445,791 B2* | 9/2016 | Stack | A61B 17/00234 |
| 9,622,897 B1* | 4/2017 | Stangenes | A61F 5/0079 |
| 10,603,095 B2* | 3/2020 | Fischer | A61B 17/00234 |
| 2003/0009085 A1* | 1/2003 | Arai | A61B 1/00089 600/127 |
| 2005/0070931 A1* | 3/2005 | Li | A61B 17/0469 606/151 |
| 2006/0241691 A1* | 10/2006 | Wilk | A61B 17/122 606/215 |
| 2006/0276810 A1* | 12/2006 | Kelleher | A61B 17/083 606/151 |
| 2007/0112362 A1* | 5/2007 | Mikkaichi | A61B 17/0487 606/153 |
| 2007/0255278 A1* | 11/2007 | Nobis | A61B 18/1445 606/45 |
| 2008/0015574 A1* | 1/2008 | Karpiel | A61B 18/1492 606/46 |
| 2008/0051627 A1* | 2/2008 | Raju | A61B 1/3132 600/104 |
| 2008/0275473 A1* | 11/2008 | Filipi | A61B 17/0625 606/145 |
| 2009/0312602 A1* | 12/2009 | Sakamoto | A61B 17/32056 600/104 |
| 2010/0145352 A1* | 6/2010 | Chang | A61B 17/00234 606/110 |
| 2010/0160934 A1* | 6/2010 | Kelleher | A61B 17/0218 606/139 |
| 2010/0217151 A1* | 8/2010 | Gostout | A61B 10/02 600/565 |
| 2011/0087222 A1* | 4/2011 | Miller | A61B 18/14 606/46 |
| 2013/0090526 A1* | 4/2013 | Suzuki | A61B 1/32 600/114 |
| 2013/0338680 A1* | 12/2013 | Harris | A61F 5/0086 606/139 |
| 2014/0148828 A1* | 5/2014 | Ewers | A61B 17/0625 606/153 |
| 2014/0214063 A1* | 7/2014 | Miyamoto | A61B 17/3205 606/167 |
| 2014/0288584 A1* | 9/2014 | De La Mora Levy | A61B 17/0218 606/170 |
| 2014/0358166 A1* | 12/2014 | Kelleher | A61B 17/0485 606/148 |
| 2015/0190166 A1* | 7/2015 | Mitelberg | A61B 17/068 606/142 |
| 2017/0238916 A1* | 8/2017 | Beaven | A61B 17/0057 |
| 2017/0304099 A1* | 10/2017 | Keren | A61B 17/00234 |
| 2019/0290325 A1* | 9/2019 | Goto | A61B 17/062 |
| 2019/0343528 A1* | 11/2019 | Fleury | A61B 17/1114 |

\* cited by examiner

PROCEDURE FOR ENDOSCOPIC FULL-THICKNESS RESECTION

BACKGROUND OF THE INVENTION

Field of the Invention

The present invention relates to a procedure for endoscopic full-thickness resection for endoscopically resecting a part of the digestive tract over the entire layer.

Description of the Related Art

Conventionally, a procedure is known in which an endoscope and a laparoscope are combined to resect a part of the digestive tract over the entire layer.

In order to further reduce the invasiveness of the patient, it is examined to perform full-thickness resection using only the endoscope.

Japanese Unexamined Patent Application, First Publication No. 2007-29195 describes a method of resecting the digestive tract over the entire layer using an endoscope and a chamber. In this method, a part of the digestive tract is drawn into the chamber over the entire layer, and a loop of high frequency snare is applied to the drawn digestive tract to resect.

SUMMARY

The present invention provides a method of resecting entire layers of a digestive tract, including: an insertion step of inserting an endoscope into the digestive tract; an everting step performed after the insertion step, to suture mucosal layers located on both sides of a target region including a lesion, cover the target region with the mucosal layers, and evert a tract wall including the target region to a side of an abdominal cavity, in the digestive tract; and an incision step performed after the everting step, to position an incision tool between the target region and the mucosal layers to incise the tract wall around the lesion by the incision tool.

DETAILED DESCRIPTION OF THE PREFERRED EMBODIMENTS

An embodiment of the present invention will be described with reference to FIGS. 1 to 11.

In the case of performing a full-thickness resecting method of the digestive tract according to the present embodiment (hereinafter simply referred to as "full-thickness resection method"), the operator first inserts the endoscope from the patient's mouth or anus (insertion step), and moves the distal end portion of the endoscope to the vicinity of the target region to be resected. As the endoscope, a commonly known flexible endoscope can be used.

Figure 1:
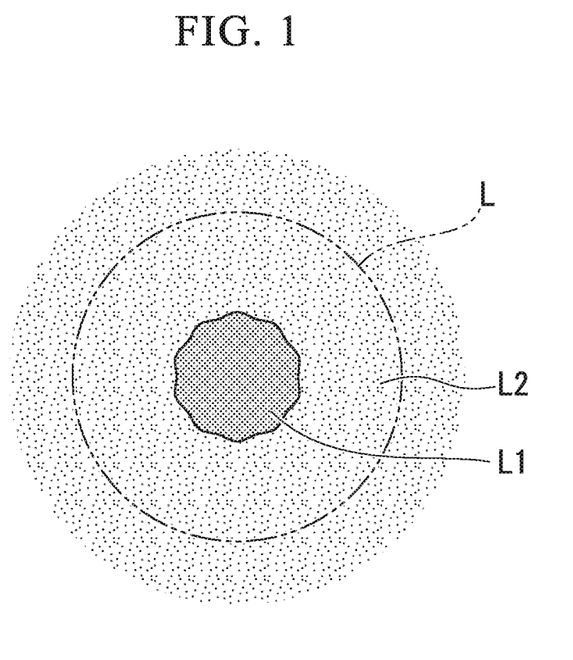
FIG. 1 is a view showing an example of a target region.

FIG. 1 shows an example of a target region. The target region L has a lesion L1 and a peripheral tissue L2 positioned around the lesion L1. The peripheral tissue L2 has a role of a margin for resecting the lesion L1 without directly contacting with the lesion L1. While observing the lesion L1 with the endoscope, the operator judges the necessary size of the peripheral tissue and determines the range of the target region L.

As the lesion L1, gastrointestinal stromal tumor (GIST), malignant tumor of the digestive tract reaching the muscle layer, and the like can be exemplified.

Figure 2:
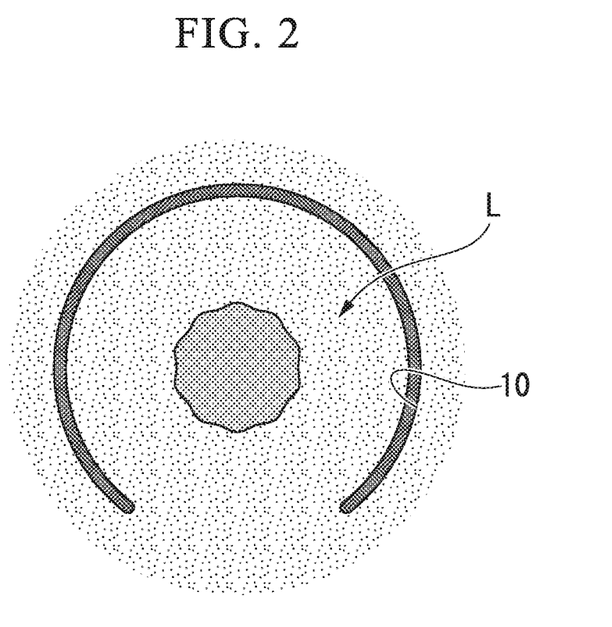
FIG. 2 is a view showing a state in which a cut end is formed by a cut end forming step of a full-thickness resection method according to an embodiment of the present invention.

Next, the operator incises the mucosal layer around the target region L to form the cut end 10 in the mucosal layer around the target region L as shown in FIG. 2 (cut end forming step). The incision of the mucosal layer can be performed using a commonly known endoscopic treatment instrument. The range that forms the cut end 10 in the periphery of the target region L may be appropriately set. For example, it may be formed in a range that does not cover the entire periphery of the target region L (for example, a part excluding a side closer to the endoscope than the side endoscope (hereinafter referred to as "front side")) or may be formed at the entire periphery of the target region L.

Next, the operator removes the submucosal layer with a generally constant peel width W1 (see FIG. 3) without resecting the mucosal layer away from the target region L (leaving the mucosal layer) than the cut end 10 to separate the mucosal layer and the muscle layer (separation step). This peeling can be performed in the same procedure as peeling in endoscopic submucosal dissection (ESD), for example.

Figure 3:
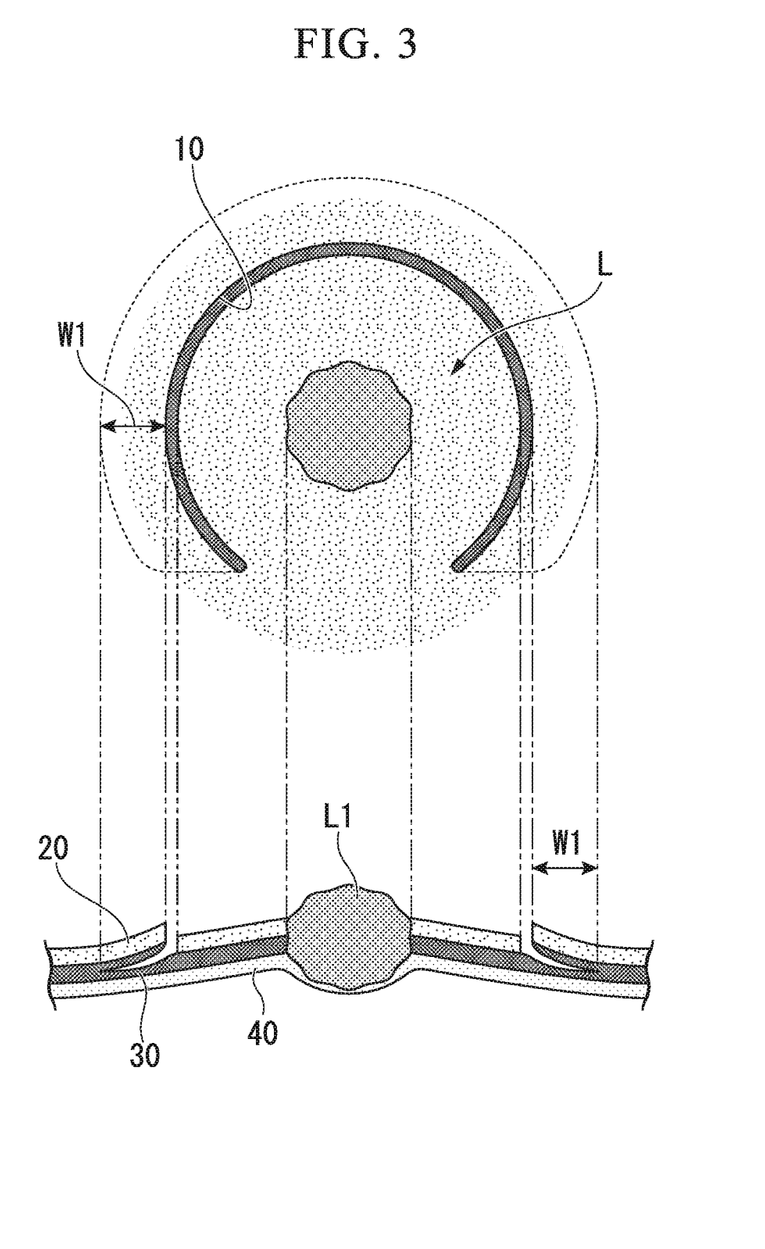
FIG. 3 is a view showing a state in which a mucosal layer and a muscle layer are separated by a separation step of the full-thickness resection method.

FIG. 3 shows the target region L and its surroundings after peeling the mucous membrane. As shown in FIG. 3, the mucosal layer 20 around the target region L is separated from the muscle layer 40 in the range of the peel width W1. The peel width W1 can be appropriately set in consideration of form or the like of the lesion L1 and is preferably about the same as the diameter of the endoscope to be used.

Figure 4:
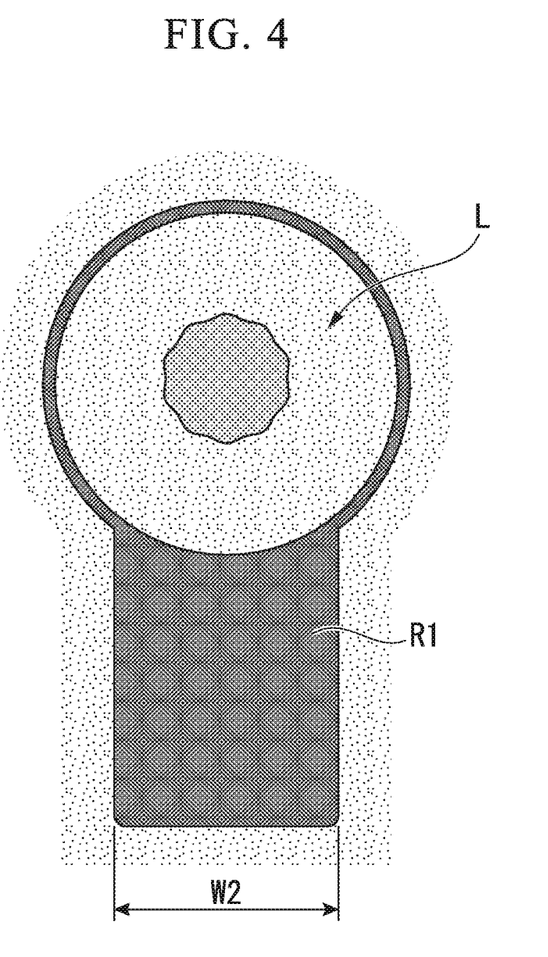
FIG. 4 is a view showing a state in which a mucous membrane defect region is formed in a part of the periphery of a target region.

Next, the operator resects the mucosal layer between the target region L and a position away from the target region L over a predetermined length and width, and forms a mucous membrane defect region R1 between the target region L and a position away from the target region L. FIG. 4 shows a state in which the mucous membrane defect region R1 is formed on the front side of the target region L as an example. This procedure can be done in the same way as ESD or endoscopic mucosal resection (EMR), for example.

The width W2 of the mucous membrane defect region R1 defines the size of the tunnel described later. The value of the width W2 is preferably the same as or slightly longer than the length of the outer periphery of the insertion portion of the endoscope to be used.

Figure 5:
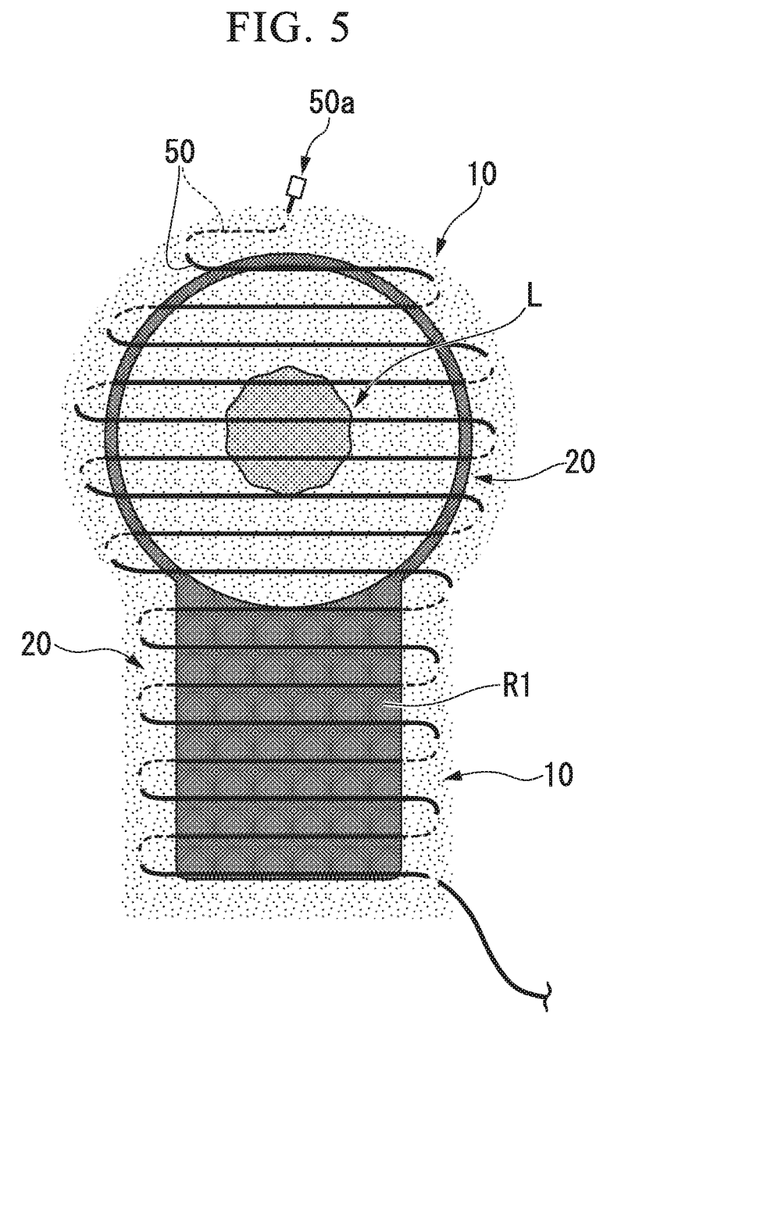
FIG. 5 is a view showing a state in which a thread is wrapped around tissue of a target tissue.

Next, as shown in FIG. 5, the operator hooks the thread 50 to the mucosal layer 20 around the target region L and hooks the thread 50 to the mucosal layer 20 facing the mucous membrane defect region R1. The end portion 50a of the thread 50 is locked so as not to slip off the tissue.

In FIG. 5, the same thread is hooked to the mucosal layer around the target region L and the mucosal layer around the mucous membrane defect region R1, but different threads may be hooked.

Thereafter, when the operator tows the thread 50, the cut ends which are positioned across the target region L come close to each other, and the mucosal layer 20 is sutured so as to cover the target region L.

Figure 6:
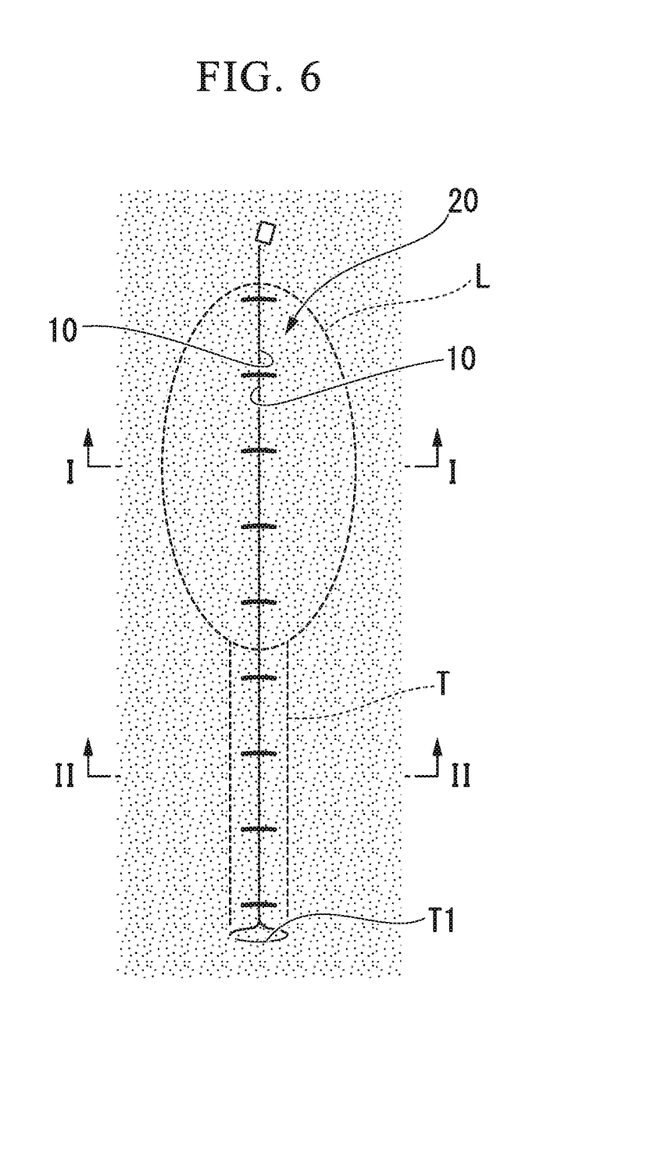
FIG. 6 is a view of a target region everted toward the side of the abdominal cavity by an everting step of the full-thickness resection method, seen from the side of the lumen of the digestive tract.
Figure 7:
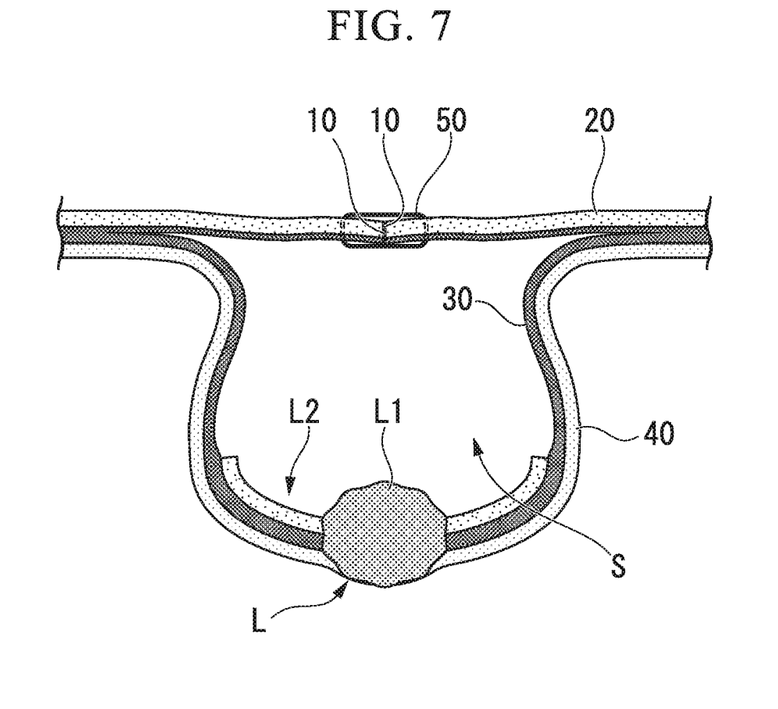
FIG. 7 is a cross-sectional view taken along the line I-I of FIG. 6.
Figure 8:
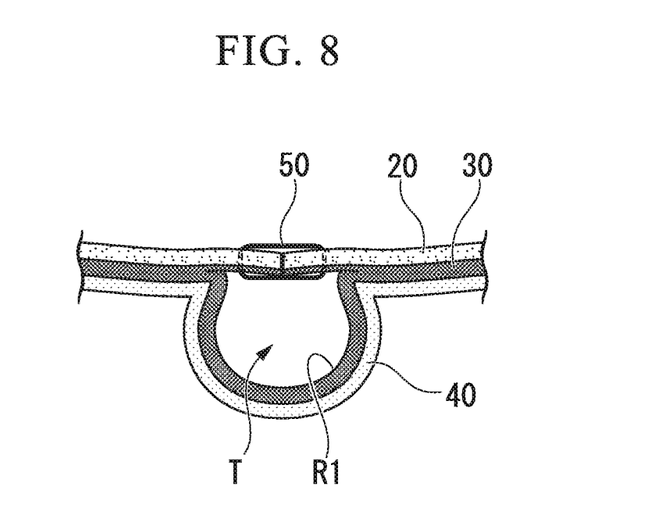
FIG. 8 is a cross-sectional view taken along the line II-II of FIG. 6.

FIGS. 6 to 8 show the state in which the mucosal layers 20 are sutured together. FIG. 7 is a cross-sectional view taken along line I-I of FIG. 6. FIG. 8 is a cross-sectional view taken along line II-II of FIG. 6. At the portion where the cut ends 10 are in contact with each other by suturing, the cut ends 10 which have been separated before suturing are sticked so that the tract wall including the target region L is everted to the abdominal cavity side (protruding to the abdominal cavity side) (everting step). At this time, it is preferable that the cut ends 10 that are separated before the suturing are sticked because the wound healing after the procedure at the cut end portion is promoted. Further, the submucosal layer 30 and the muscle layer 40 around the target region L peeled from the mucosal layer 20 are separated from the mucosal layer 20, whereby a space S is formed between the sutured mucosal layer 20 and the target region L (space forming step).

As the mucosal layers 20 on both sides of the mucous membrane defect region R1 are sutured together, the mucous membrane defect region R1 is also covered by the mucosal layer 20 and protrudes slightly to the abdominal cavity side as shown in FIGS. 6 and 8. As a result, a tunnel T extending along the tract wall of the digestive tract is formed. The tunnel T has an opening T1 (see FIG. 6) at a position distant from the target region L and communicates with the space S. Therefore, the endoscope inserted in the opening T1 can reach the target region L through the tunnel T.

Figure 9:
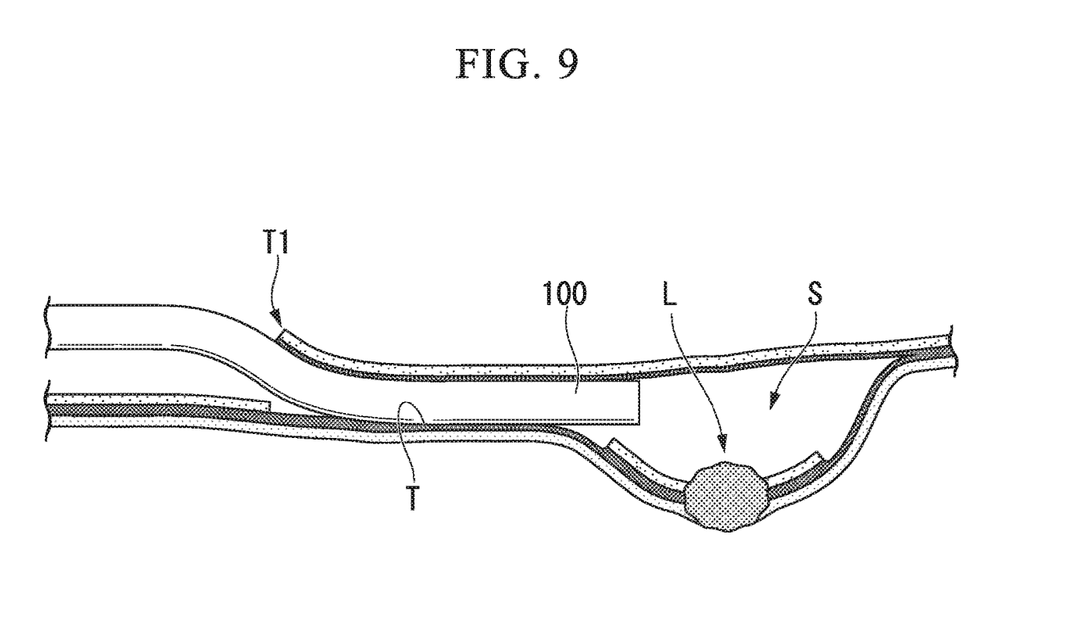
FIG. 9 is a view showing how the endoscope enters between a mucosal layer and a muscle layer in an entering step of the full-thickness resection method.

The operator inserts the endoscope into the opening T1 and causes the distal end portion of the endoscope 100 to enter the space S as shown in FIG. 9 (entering step). The operator observes the target region L with the endoscope 100 and determines the position of the incision line for separating the tissue of the target region L from the digestive tract.

Figure 10:
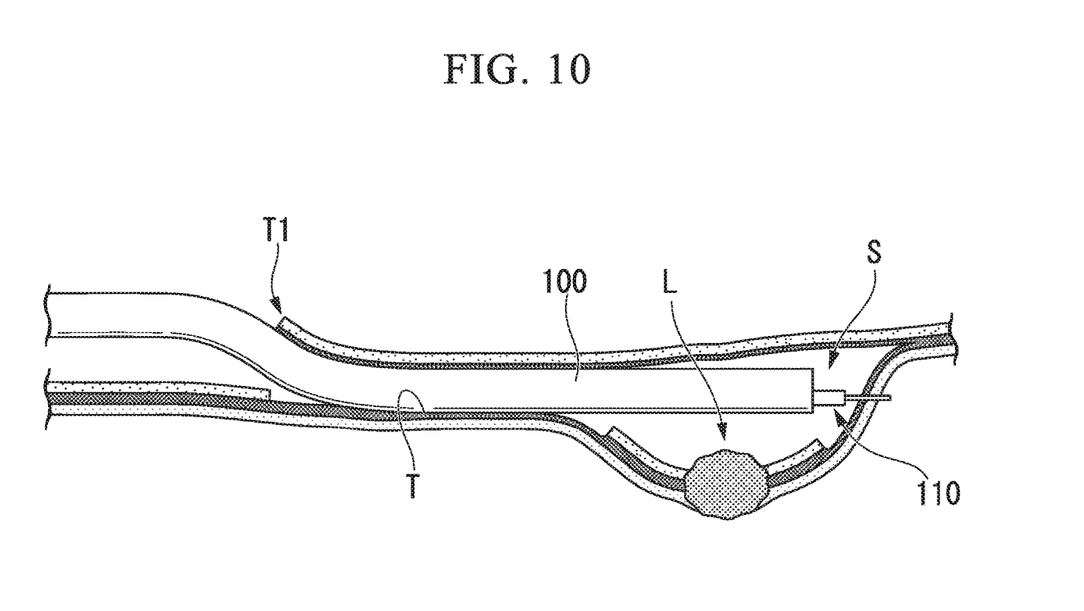
FIG. 10 is a view showing a state in which a submucosal layer and a muscle layer around a target tissue are incised by an incision tool in an incision step of the full-thickness resection method.
Figure 11:
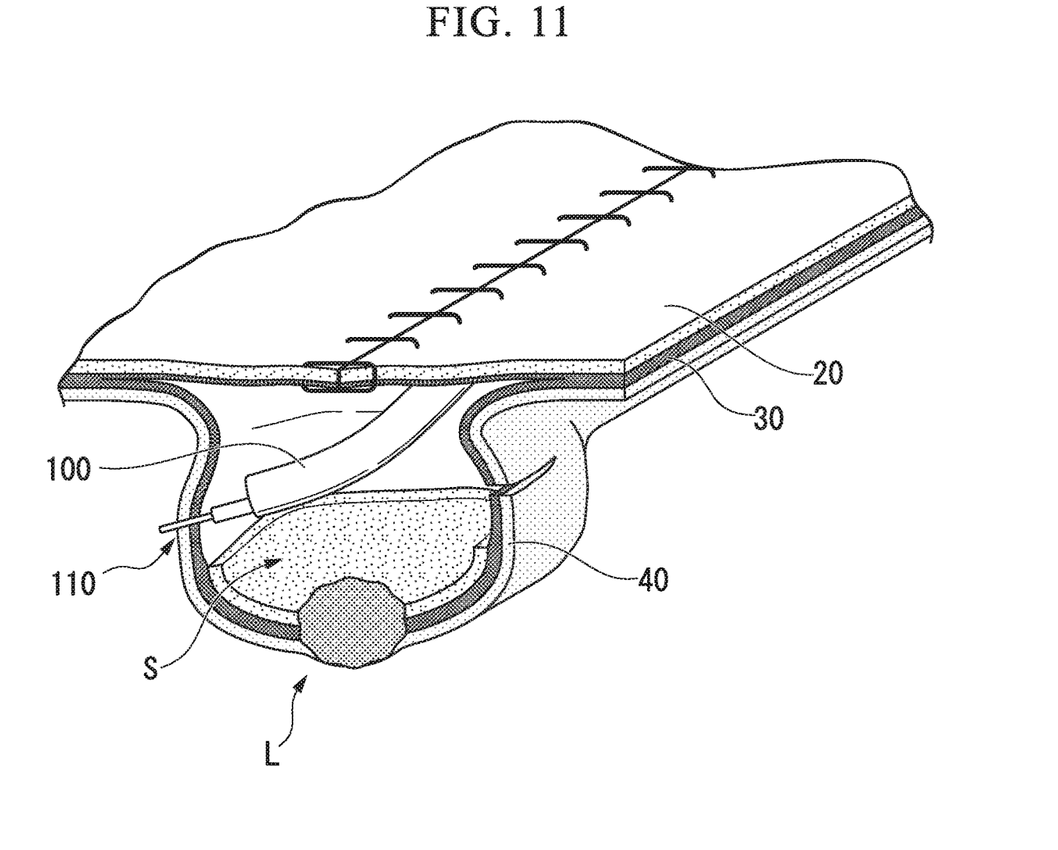
FIG. 11 is a view showing a state in which a submucosal layer and a muscle layer around a target tissue are incised by an incision tool in an incision step of the full-thickness resection method.

Subsequently, as shown in FIG. 10, the operator causes the incision tool 110 such as a high frequency knife inserted in the treatment instrument channel (not shown) of the endoscope 100 to protrude from the endoscope 100. Then, while observing the target region L with the endoscope 100, as shown in FIGS. 10 and 11, the submucosal layer 30 and the muscle layer 40 around the target region L are incised with the incision tool 110 located in the space S (incision step). This incision may be performed while appropriately bending the endoscope 100. From the viewpoint of workability of incision, it is preferable to start incision from a position far from the endoscope (far side) around the lesion. Note that this is not essential, and incision may be performed from a position close to the endoscope (near side) around the lesion.

When the submucosal layer 30 and the muscle layer 40 (including the serosa) are incised, the wall of the digestive tract is incised throughout the entire layer and a hole communicating with the abdominal cavity is opened. However, since the mucosal layer 20 located above the target region L is closed by suturing and the tunnel T communicating with the space S is closed with the endoscope 100, the gas stored in the digestive tract is difficult to escape to the abdominal cavity. Therefore, it is preferably suppressed that the digestive tract rapidly collapses (collapses) as the incision proceeds. When the inner diameter of the tunnel T and the outer diameter of the endoscope 100 are about the same, the gas hardly escapes, and the collapse suppression effect is further enhanced.

Figure 12:
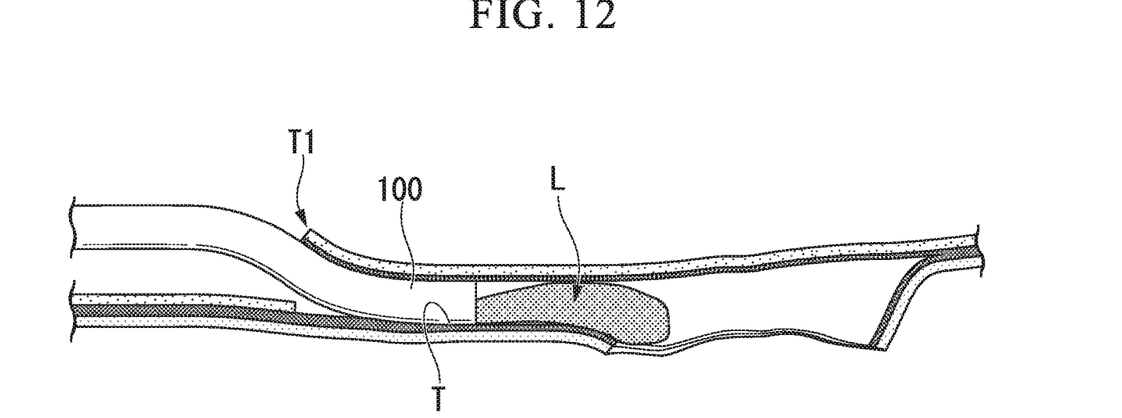
FIG. 12 is a view showing a state in which tissue is collected that is resected in a collection step of the full-thickness resection method.

After the tissue surrounding the target region L is incised substantially over the entire circumference, suction is performed with the endoscope, and the remaining tissue is dissected while sucking the tissue of the target region L to the endoscope. As a result, it is possible to separate the tissue from the digestive tract without dropping the tissue. When the endoscope 100 is moved backward while sucking the tissue of the target region L to the endoscope, it is possible to collect the tissue of the target region L outside the body passing through the tunnel T as shown in FIG. 12 (collection step).

Figure 13:
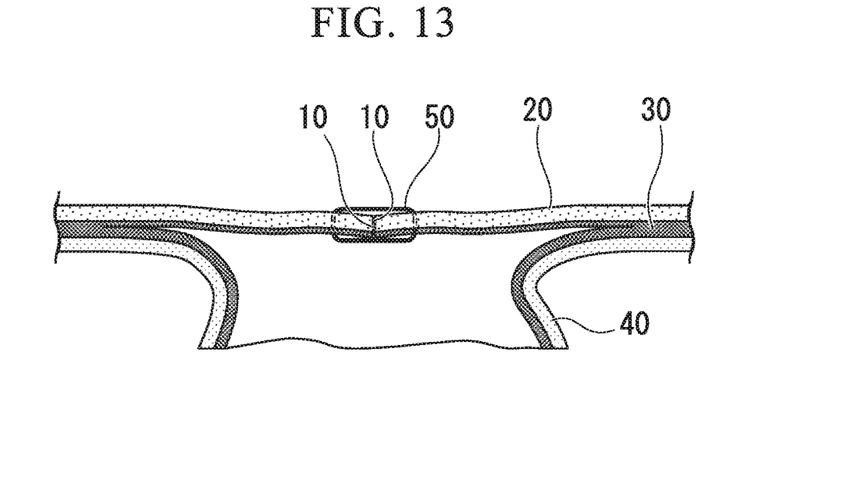
FIG. 13 is a view showing a digestive tract from which tissue has been resected.

Finally, when the opening T1 is closed using suturing threads, clips or the like, the full-thickness resection method of this embodiment is completed. The digestive tract after completion of the full-thickness resection is shown in FIG. 13.

A high frequency snare may be used for separating the target region L. In this case, it is possible to grasp the lesion with the snare while incising it and collect the target region L outside the body.

When using an endoscope having two channels, it is possible to collect the lesion outside the body by inserting a grasping forceps into a channel different from the channel through which the high frequency knife is passed and separating the target region L from the digestive tract while grasping the lesion with the grasping forceps.

As described above, according to the full-thickness resection method of the present embodiment, it is possible to perform full-thickness resection of a part of the digestive tract by using the endoscope 100 and the incision tool 110 inserted from a natural opening such as a mouth. Therefore, it is not necessary to drill holes in the abdominal wall, and patient invasion can be further reduced as compared with the full-thickness resection using a laparoscope.

In the case of performing full-thickness resection only with a medical device introduced from a natural opening, the treatment of a hole formed by resection is the most difficult. When a hole communicating with the abdominal cavity is formed in the digestive tract, gas in the digestive tract will immediately begin to leak into the abdominal cavity. If the digestive tract collapses due to leakage of gas, both of observation with the endoscope and procedure of closing the hole become very difficult.

In the full-thickness resection method of this embodiment, since the mucosal layer 20 is sutured before entire layer of the surrounding of the target region L is incised, even if a hole is formed in the digestive tract afterwards, the gas in the digestive tract will not leak rapidly into the abdominal cavity. Furthermore, since the mucosal layers 20 are sutured together before separating the target region L, it is not necessary to perform a difficult procedure such as suturing after separating the target region L.

Even with the method described in Japanese Unexamined Patent Application, First Publication No. 2007-29195, it is possible to perform full-thickness resection using only medical devices introduced from natural openings. However, in this method, since entire layers are incised at the same time with respect to the tissue drawn into the chamber, "layer misalignment" in which the mucosal layer and the muscle layer or the like move relative to each other in the surface direction may occur in the tissue at incision. When layer misalignment occurs, even if sufficient margins are secured in the mucosal layer, there is no guarantee that a similar margin will be secured in the submucosal layer or muscle layer, so it is necessary to enlarge the peripheral tissue of the target region in order to ensure a sufficient margin. As a result, the target region to be resected becomes large, and it is difficult to reduce the invasiveness of the patient.

In the present embodiment, in the mucosal layer 20, the cut end 10 is formed while securing a sufficient margin for the lesion L1. Thereafter, the mucosal layer 20 around the target region L is peeled off from the submucosal layer 30, and the submucosal layer 30 and the muscle layer 40 around the target region L are incised in the space S. Therefore, since the layer misalignment does not occur at the time of incision of the submucosal layer 30 and the muscle layer 40, it is not necessary to enlarge the peripheral tissue L2 excessively, and the amount of margin can be minimized to further reduce the invasiveness of the patient.

In the present embodiment, an example in which the mucous membrane defect region R1 is formed to form the tunnel T has been described, but the method of forming the tunnel is not limited thereto.

Figure 14:
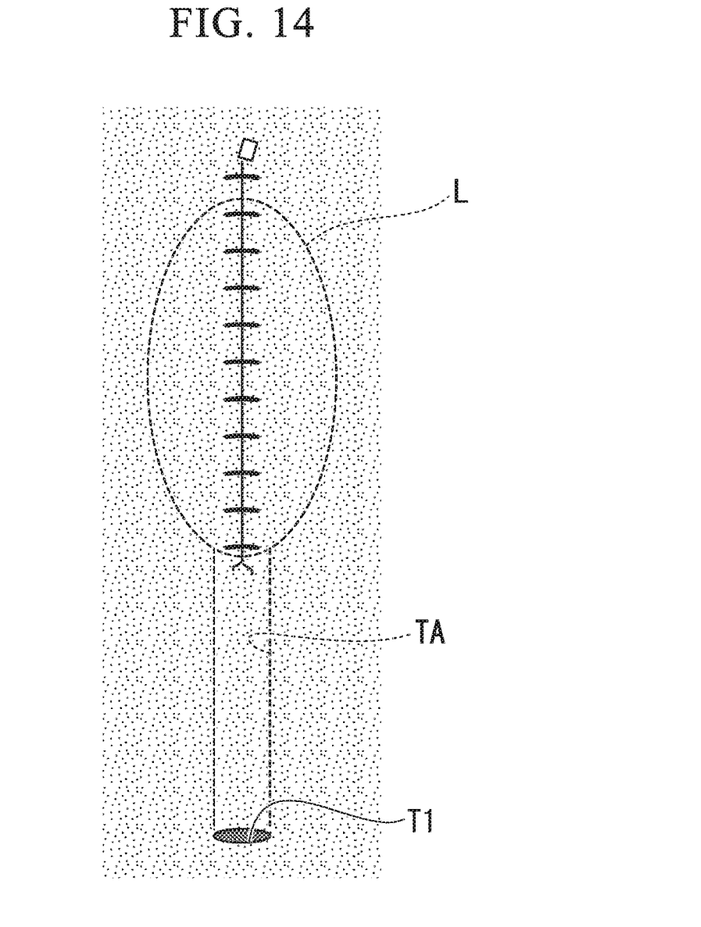
FIG. 14 is a view showing another example of a tunnel in the full-thickness resection method.

The tunnel TA shown in FIG. 14 is formed by forming an incision having a depth reaching the submucosal layer at the position of the tract wall where the opening T1 is desired to be formed, inserting the endoscope into the incision site, and using a high frequency knife inserted into the channel of the endoscope. By energizing the high frequency knife while advancing the endoscope, it is possible to form the tunnel TA reachable to the target region L while separating the submucosal layers from each other, or between the mucosal layer and the submucosal layer.

By forming the tunnel in this manner, it is not necessary to suture the mucosal layers of the tunnel portion in the everting step, thereby the procedure is further simplified.

Although the embodiment of the present invention has been described above, the technical scope of the present invention is not limited to the above embodiment, and it is possible to change the combination of constituent elements and to make various changes to each constituent element or delete them within the scope not deviating from the spirit of the present invention.

For example, the collection step may be performed using tagged suturing threads or instruments other than grasping forceps such as snare loops or the like.

In the full-thickness resection method of the present invention, it is not essential to form a tunnel. For example, when the size of the lesion L1 is small and the range of the peripheral tissue L2 is sufficiently wide, the incision step may be executed by leaving an un-sutured portion when suturing the mucosal layers around the target region and causing the endoscope enter the space from the un-sutured portion.

In the full-thickness resection method of the present invention, in the case where it is possible to ensure a sufficient space to perform sufficient treatment with the incision tool 110 in the everting step, the above-described separated end forming step and separation step are not essential.

What is claimed is:

1. A method of resecting entire layers of a digestive tract, comprising:
   inserting an endoscope into the digestive tract, the digestive tract comprising a tract wall that includes a mucosal layer, a muscle layer, and a target region including a lesion;
   then suturing areas of the mucosal layer that are located on both sides of the target region so as to: (i) cover the target region with the sutured areas of the mucosal layer, and (ii) evert a portion of the tract wall including the target region to a side of an abdominal cavity with a space being formed between the target region and the sutured areas of the mucosal layer;
   inserting the endoscope into the space; and
   incising the tract wall around the lesion by an incision tool that is positioned between the target region and the sutured areas of the mucosal layer after the portion of the tract wall is everted to the side of the abdominal cavity, the incising including:
      causing the incision tool to protrude from a channel of the endoscope that has entered into the space; and
      incising the muscle layer around the target region with the incision tool while observing the target region with the endoscope.

2. The method according to claim 1, further comprising before suturing the areas of the mucosal layer:
   incising the mucosal layer around the target region so as to form cut ends; and
   separating the mucosal layer around the cut ends from the muscle layer without resection, and
   wherein:
      the areas of the mucosal layer are sutured in a state in which the cut ends sandwiching the target region therebetween are stuck together, and
      the incision of the tract wall around the lesion includes incising the muscle layer and serosa around the target region with the incision tool inserted in the space to separate the target region from the digestive tract.

3. The method according to claim 1, further comprising:
   forming a tunnel extending along the tract wall in communication with the space and having an opening at a location remote from the space,
   wherein the endoscope is inserted into the space through the opening and the tunnel.

4. The method according to claim 3, wherein:
   the forming of the tunnel includes:
      resecting the mucosal layer of the tract wall at a position located between the target region and a position away from the target region to form a mucous membrane defect region; and
      suturing opposing portions of the mucosal layer that sandwich the mucous membrane defect region therebetween to cover the mucous membrane defect region.

5. The method according to claim 4, further comprising:
separating the lesion from the digestive tract and collecting the lesion via the tunnel.

6. A method of resecting entire layers of a digestive tract, comprising:
inserting an endoscope into the digestive tract, the digestive tract including a tract wall that includes:
a target region including a lesion, and
a first region and a second region that are located on both sides of the target region;
then suturing together a mucosal layer of the first region and a mucosal layer of the second region without suturing a muscle layer of the first region or a muscle layer of the second region such that the target region, the muscle layer of the first region, and the muscle layer of the second region are everted to an abdominal cavity side of the mucosal layer of the first region and the mucosal layer of the second region; and
then incising the tract wall around the lesion by an incision tool, which is positioned between: (i) the target region and (ii) the mucosal layer of the first region and the mucosal layer of the second region, by incising the muscle layer of the first region or the muscle layer of the second region, which are positioned on the abdominal cavity side of the mucosal layer of the first region and the mucosal layer of the second region.

7. The method according to claim 6, wherein:
a space is formed between the target region and the mucosal layer of the first region and the mucosal layer of the second region when the target region, the muscle layer of the first region, and the muscle layer of the second region are everted to an abdominal cavity side of the mucosal layer of the first region and the mucosal layer of the second region.

8. The method according to claim 7, further comprising:
inserting the endoscope into the space,
wherein the incising of the tract wall includes:
causing the incision tool to protrude from a channel of the endoscope that has entered the space, and
incising the muscle layer of the first region or the muscle layer of the second region with the incision tool while observing the target region with the endoscope.

9. The method according to claim 8, further comprising before suturing the first region and the second region:
incising the mucosal layer of the first region and the mucosal layer of the second region around the target region so as to form cut ends; and
separating the mucosal layer of the first region and the mucosal layer of the second region around the cut ends from the muscle layer of the first region and the muscle layer of the second region, respectively, without resection,
wherein:
the mucosal layer of the first region is sutured to the mucosal layer of the second region in a state in which the cut ends sandwiching the target region therebetween are stuck together, and
the incision of the tract wall around the lesion includes incising the muscle layer of the first region or the muscle layer of the second region and serosa around the target region with the incision tool inserted in the space to separate the target region from the digestive tract.

10. The method according to claim 8, further comprising:
forming a tunnel extending along the tract wall in communication with the space and having an opening at a location remote from the space,
wherein the endoscope is inserted into the space through the opening and the tunnel.

11. The method according to claim 10, wherein:
the forming of the tunnel includes:
resecting the mucosal layer of the tract wall at a position located between the target region and a position away from the target region to form a mucous membrane defect region; and
suturing opposing portions of the mucosal layer that sandwich the mucous membrane defect region therebetween to cover the mucous membrane defect region.

12. The method according to claim 11, further comprising:
separating the lesion from the digestive tract and collecting the lesion via the tunnel.

* * * * *